(12) United States Patent
Sarin et al.

(10) Patent No.: US 8,829,444 B2
(45) Date of Patent: Sep. 9, 2014

(54) SYNTHESIS OF ADVANCED SCINTILLATORS VIA VAPOR DEPOSITION TECHNIQUES

(71) Applicant: Trustees of Boston University, Boston, MA (US)

(72) Inventors: Vinod K. Sarin, Boston, MA (US); Stephen Gibson Topping, Brighton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 14/014,561

(22) Filed: Aug. 30, 2013

(65) Prior Publication Data

US 2013/0341513 A1   Dec. 26, 2013

Related U.S. Application Data

(63) Continuation of application No. 12/700,210, filed on Feb. 4, 2010, now Pat. No. 8,530,845.

(60) Provisional application No. 61/149,880, filed on Feb. 4, 2009.

(51) Int. Cl.

| | |
|---|---|
| *G01T 3/06* | (2006.01) |
| *C23C 16/40* | (2006.01) |
| *C09K 11/77* | (2006.01) |
| *G21K 4/00* | (2006.01) |
| *A61B 6/00* | (2006.01) |
| *C23C 14/08* | (2006.01) |
| *C23C 14/35* | (2006.01) |

(52) U.S. Cl.
CPC ............. *C09K 11/7787* (2013.01); *C23C 16/40* (2013.01); *G21K 4/00* (2013.01); *A61B 6/42* (2013.01); *G21K 2004/06* (2013.01); *C23C 14/08* (2013.01); *C23C 14/35* (2013.01)
USPC ................................ 250/361 R; 252/301.4 R

(58) Field of Classification Search
CPC ............................... G01T 3/06; C09K 11/7787
USPC ........... 250/361 R; 252/301.4 R; 427/255.28, 427/163.2
See application file for complete search history.

(56) References Cited

U.S. PATENT DOCUMENTS

2009/0008561 A1* 1/2009 Nagarkar et al. ......... 250/361 R

OTHER PUBLICATIONS

Shestakova et al., "A new scintillator structure for thermal neutron imaging", Nuclear Instruments and Methods in Physics Research B, vol. 263 (2007), pp. 234-238.

(Continued)

*Primary Examiner* — David Porta
*Assistant Examiner* — Faye Boosalis
(74) *Attorney, Agent, or Firm* — Preti Flaherty Beliveau & Pachios LLP

(57) ABSTRACT

Transparent optical ceramic coating materials have been fabricated from europium-doped lutetium oxide ($Lu_2O_3$:Eu) using physical vapor deposition and chemical vapor deposition techniques. The non-pixilated film coatings have columnar microcrystalline structure and excellent properties for use as radiological scintillators, namely very high density, high effective atomic number, and light output and emission wavelength suitable for use with silicon-based detectors having a very high quantum efficiency. The materials can be used in a multitude of high speed and high resolution imaging applications, including x-ray imaging in medicine.

21 Claims, 17 Drawing Sheets

(56) References Cited

OTHER PUBLICATIONS

Farman et al., "Effects of scintillator on the modulation transfer function (MTF) of a digital imaging system", Oral Surg., Oral Med., Oral Pathol., Oral Radiol. & Endod., vol. 99 (2005), pp. 608-613.

Trojan-Piegza et al., "Comparison of spectroscopic properties of nanoparticulate $Lu_2O_3$:Eu synthesized using different techniques", Journal of Alloys and Compounds, vol. 380 (2004), pp. 123-129.
Zych, "Concentration dependence of energy transfer between $Eu^{3+}$ ions occupying two symmetry sites in $Lu_2O_3$", Journal of Physics: Condensed Matter, vol. 14 (2002), pp. 5637-5650.

* cited by examiner

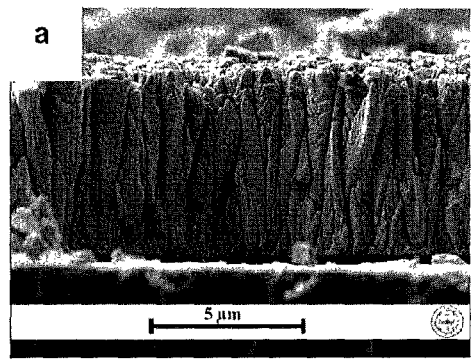
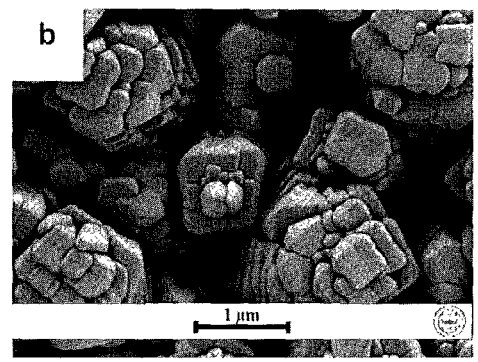
FIG. 9A  FIG. 9B
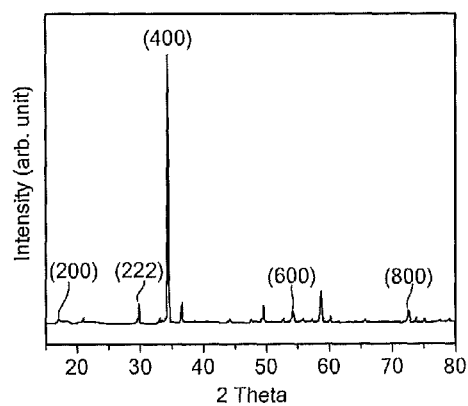
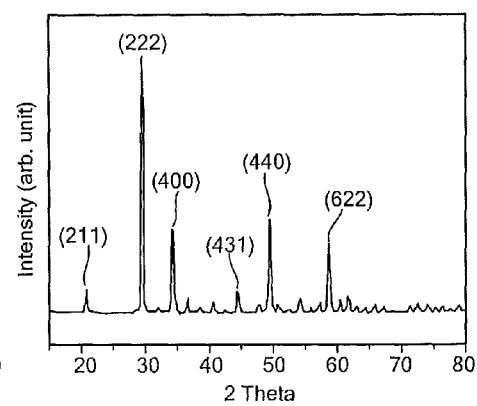
FIG. 10A  FIG. 10B

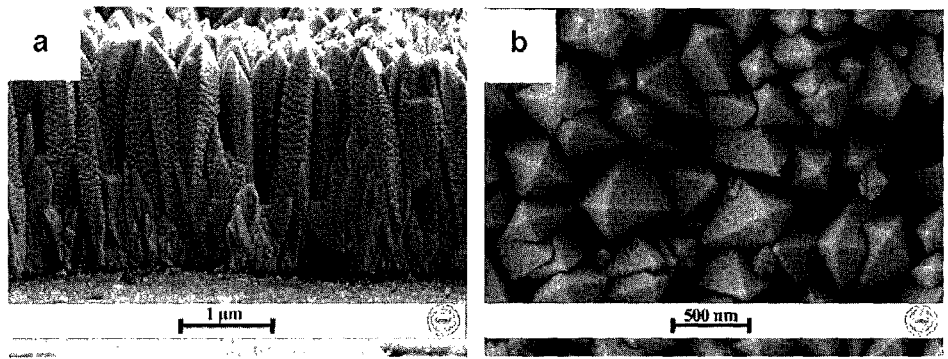
FIG. 11A  FIG. 11B
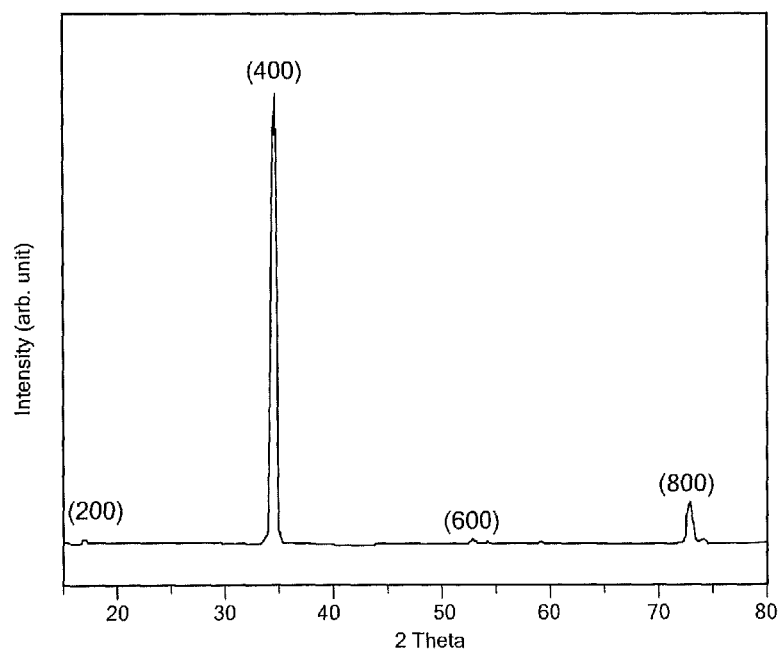
FIG. 12

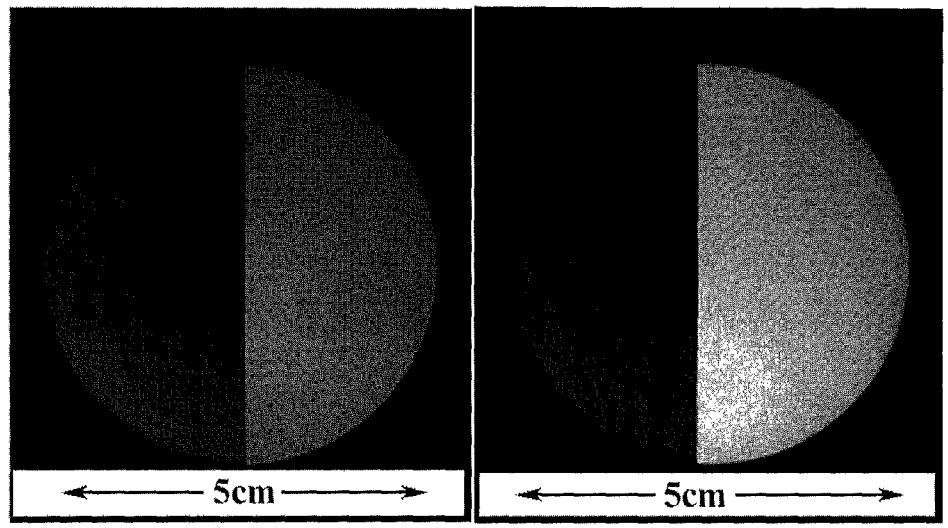
FIG. 18A   FIG. 18B
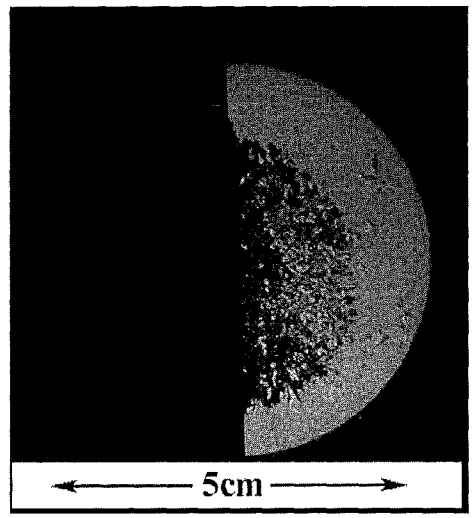
FIG. 18C

SYNTHESIS OF ADVANCED SCINTILLATORS VIA VAPOR DEPOSITION TECHNIQUES

CROSS REFERENCE TO RELATED APPLICATIONS

This application claims the benefit under 35 U.S.C. §119 (e) of U.S. Provisional Application No. 61/149,880 filed Feb. 4, 2009, the entire disclosure of which is incorporated herein by reference.

This application claims the benefit under 35 U.S.C. §120 of U.S. application Ser. No. 12/700,210, filed Feb. 4, 2010, the entire disclosure of which is incorporated herein by reference.

STATEMENT REGARDING FEDERALLY SPONSORED RESEARCH OR DEVELOPMENT

The research leading to this invention was carried out with U.S. Government support provided under Grant No. 5R21EB005037 from the National Institutes of Health. The U.S. Government has certain rights in the invention.

BACKGROUND

Rare earth oxides are used in the x-ray detector industry due to their stability, high density, and high atomic number. However, they have generally been limited to small area detectors due to manufacturing limitations. The present industry standard scintillator for x-ray detection is cesium iodide doped with tantalum (CsI:Tl). In terms of optical and scintillation properties, CsI:Tl has good transparency, a density of 4.51 g/cc, and emits 60,000 photons per MeV of incident x-rays [1]. Lutetium Oxide doped with Europium Oxide ($Lu_2O_3$:Eu) has been studied as an alternative to CsI:Tl, because its high density and high atomic number make it an ideal scintillator. $Lu_2O_3$:Eu has a highly transparent body-centered cubic (BCC) crystal structure, a density of 9.4 g/cc, and it emits 30,000 photons per MeV [2].

Current manufacturing methods, such as sintering and hot pressing, produce a transparent 2-3 mm thick disc that must be ground and polished to a thickness close to the desired thickness. In order to reduce light scattering, the disc must then be pixelized as shown in FIG. 1 using a highly labor intensive laser ablation process. The top surface is then placed onto a CCD camera using optical glue, and the back is ground off [1]. Use of $Lu_2O_3$:Eu scintillators in dentistry, which is one of the potential applications for such a material, would require a ceramic detector of approximately 200 microns thickness in order to absorb most of the incoming x-rays, compared to 2 mm thickness for CsI. With current fabrication technology, this is not commercially viable, due to the required processing. There is a need for improved methods of manufacturing $Lu_2O_3$:Eu scintillator material that would be more efficient, less labor intensive, and more suitable to produce large area scintillators than with currently available techniques.

SUMMARY OF THE INVENTION

The invention provides scintillator coating materials and films that provide superior radiological imaging. The materials are based on lutetium (e.g., $Lu_2O_3$, $Lu_2SiO_5$, etc.), which has a high atomic number and is therefore highly efficient at capturing high energy photons, such as x-rays. The lutetium is in the form of, for example, lutetium oxide ($Lu_2O_3$) doped with europium oxide ($Eu_2O_3$). The lutetium oxide and europium oxide form a solid solution having an oriented columnar grain growth pattern. Lutetium serves to trap incident x-rays, whose energy is transferred to europium, causing an electron orbital shift in europium that results in the release of visible light photons. The columnar growth structure eliminates the need for pixelation and provides highly efficient light transmission out of the scintillator material. The emitted visible light is in a wavelength range that can be imaged with high efficiency using solid state silicon devices such as CCDs.

One aspect of the invention is a method of preparing a radiological scintillator coating material by physical vapor deposition (PVD). The method includes the steps of providing a target and a substrate to be coated with the scintillator coating material and subjecting the target to a physical vapor deposition process. The substrate is formed from a compressed powder of $Lu_2O_3$ doped with about 5-15 mol % $Eu_2O_3$. In some embodiments, the PVD method is plasma sputtering in a radio frequency magnetron sputtering system using an argon plasma. As a result of the physical deposition process, a scintillator coating comprising $Lu_2O_3$ and $Eu_2O_3$ is deposited onto the substrate. In some embodiments, the method further includes the step of annealing the scintillator coating by heat treatment at a temperature in the range of about 100 to 1400° C.

Another aspect of the invention is a method of preparing a radiological scintillator coating material by chemical vapor deposition (CVD). The method includes the steps of providing chemical reactants and a substrate to be coated with the scintillator coating material and reacting the reactants in a CVD reactor. The reactants include $LuCl_3$, $EuCl_3$, $CO_2$, and $H_2$. As a result of the CVD process, a scintillator coating comprising $Lu_2O_3$ and $Eu_2O_3$ is deposited onto the substrate. The ratio of $LuCl_3$ and $EuCl_3$ is adjusted to provide a ratio of about 85-95 mol % $Lu_2O_3$ and about 5-15% $Eu_2O_3$ in the scintillator coating. In some embodiments, the method further includes the step of annealing the scintillator coating by heat treatment at a temperature in the range of about 100 to 1400° C. In some embodiments, the $LuCl_3$ and $EuCl_3$ reactants are generated in the reactor by reacting $Cl_2$ gas with Lu metal and Eu metal.

Yet another aspect of the invention is a non-pixilated radiological scintillator coating material including about 85 to 95 mol % $Lu_2O_3$ and about 5 to 15 mol % $Eu_2O_3$. The material has a preferentially oriented columnar grain growth structure, absorbs electromagnetic radiation including x-rays, and in response emits visible light. The material can be used in radiological imaging applications in medicine and dentistry.

Still another aspect of the invention is an x-ray imaging device. The device includes a scintillator coating material made of about 85 to 95 mol % $Lu_2O_3$ doped with about 5 to 15 mol % $Eu_2O_3$. The scintillator coating is deposited onto a substrate or a CCD imaging device. Optionally, the CCD is in turn mounted on a circuit board material such as FR4. The device can be linked to a microprocessor, a memory unit, and a display unit, such as a computer, to display images formed by x-rays impinging on the scintillator material.

BRIEF DESCRIPTION OF THE DRAWINGS

FIGS. 9A and 9B show the morphology by SEM of $Lu_2O_3$:Eu deposited by CVD with stacked platelet columnar morphology in cross section (FIG. 9A) and surface view (FIG. 9B). Growth was at 1000° C.

FIG. 10A shows the results of x-ray diffraction analysis of a stacked platelet columnar coating of $Lu_2O_3$:Eu deposited by CVD. The diffraction pattern of single phase polycrystalline lutetium oxide powder is shown in FIG. 10B for comparison.

FIGS. 11A and 11B show SEM of highly faceted columnar $Lu_2O_3$:Eu deposited by CVD in cross section (FIG. 11A) and surface view (FIG. 11B).

FIG. 12 shows an x-ray diffraction plot of highly faceted columnar $Lu_2O_3$:Eu deposited by CVD.

FIGS. 18A-18C show photoluminescence images (254 nm excitation) of PVD coatings of $Lu_2O_3$:Eu made using RF power settings of 50 W (FIG. 16A), 75 W (FIG. 16B), and 100 W (FIG. 16C). For each coating, the left half of the figure shows a coating as deposited, and the right half shows a coating that was heat treated at 900° C. for 2 hours.

DETAILED DESCRIPTION OF THE INVENTION

Figure 1:
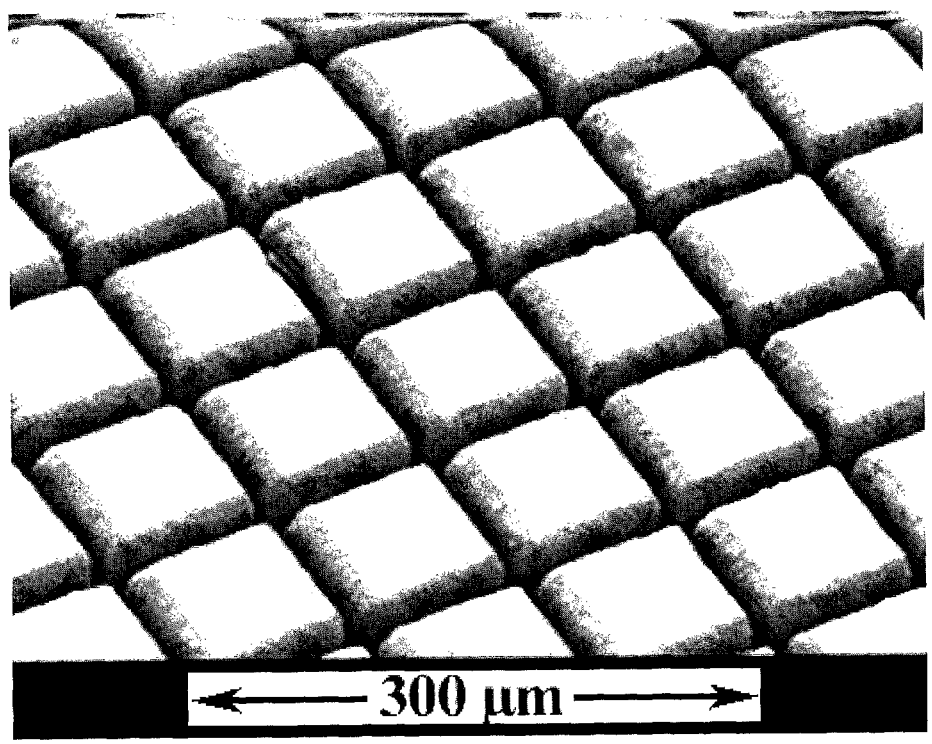
FIG. 1 shows a scanning electron micrograph of a prior art $Lu_2O_3$:Eu scintillator material that has been pixelized by laser ablation.

This application claims priority under 35 U.S.C. §119(e) to U.S. Provisional Patent Application No. 61/149,880 filed Feb. 4, 2009 and entitled "SYNTHESIS OF ADVANCED SCINTILLATORS VIA VAPOR DEPOSITION TECHNIQUES" which is incorporated by reference herein in its entirety.

This application claims the benefit under 35 U.S.C. §120 of U.S. application Ser. No. 12/700,210, filed Feb. 4, 2010, the entire disclosure of which is incorporated herein by reference.

Novel $Eu_2O_3$-doped $Lu_2O_3$ scintillator materials and methods of making them are provided by the present invention. The new materials are made by vapor deposition techniques, including physical vapor deposition (PVD) and chemical vapor deposition (CVD). The materials can be used as coatings or films and are particularly well suited to serve as scintillators for radiological imaging devices, allowing the real time acquisition of images in digital form. The invention also provides imaging devices that incorporate the scintillator materials.

The new materials utilize high energy photon capture by lutetium, which has a high atomic number and very high density. The lutetium is present in the scintillator materials in the form of lutetium oxide ($Lu_2O_3$) that has been doped with europium oxide ($Eu_2O_3$). The lutetium oxide and europium oxide form a solid solution whose morphology reveals an oriented columnar grain structure. The europium dopant converts captured x-rays into emitted visible light photons.

The columnar grain structure of the scintillator materials eliminates the need for pixelation and provides highly efficient light transmission out of the scintillator material, similar to transmission of light in an optical fiber. By eliminating the need for pixelation, the materials of the invention avoid laborious and time-consuming steps in the production of scintillator films, and make possible the production of much larger area scintillator films than could be practically achieved using the pixelation and coating methods required for hot-pressed $Lu_2O_3$:Eu materials, in order to minimize light scattering. The size or surface area that can be achieved will depend on and be limited by the size of the target in PVD and the size of the reactor in CVD. The emitted visible light is in the 600 nm range, a range that can be imaged with high efficiency and recorded directly in digital form using CCDs.

The key to the production of the new scintillator materials is the use of vapor deposition techniques. The materials are made by either a PVD method or a CVD method. Further, in order to achieve high efficiency light emission from the scintillator materials, a post-deposition thermal annealing step is performed, which cures defects in the material, allowing efficient energy transfer resulting in light emission.

PVD methods that are suitable for synthesizing $Lu_2O_3$:Eu films with appropriate structure for use as a scintillator include, but are not limited to, evaporative deposition, cathodic arc deposition, ion bombardment, electron beam bombardment, and sputtering. In evaporation, a material is heated in a vacuum to increase its vapor pressure, resulting in deposition of the vaporized material. Arc deposition uses a high power electrical arc to vaporize a target, resulting in deposition of vaporized material. Sputtering utilizes a plasma discharge to sputter away atoms from a target material into a vapor, which are then deposited onto a substrate. Ion beam or electron bombardment use the respective beam to vaporize material from a target and deposit the vaporized material onto a substrate. A preferred PVD method is radio frequency magnetron sputtering. Phase diagrams for films deposited by a PVD process such as sputtering are known from previous studies. From such previous studies it is understood that the columnar grain structure, which is preferred for the materials of the present invention, are preferentially formed at high substrate temperatures.

Any CVD method that provides an appropriate grain morphology and Lu:Eu stoichiometry can be used to manufacture the scintillator films of the invention. CVD of films or coatings involves the chemical reaction of gaseous reactants on or near the vicinity of a heated substrate surface. This atomistic deposition method can provide high purity materials with structural control at atomic or nanometer scale level. Moreover, it can produce single layer, multilayer, composite, nanostructured, and functionally graded coating materials with well controlled dimension and unique structure at low processing temperatures. Furthermore, one of the unique features of CVD compared with other deposition techniques is its non-line-of-sight deposition capability, which allows the coating of complex shaped components.

In addition, CVD can be carried out employing hot or cold wall reactors. In hot wall CVD, the deposition chamber is heated, which in turn heats the gases through conduction and radiation. Though the hot wall reactor can provide very precise temperature control, the interior of the hot wall reactor is also coated (heterogeneous nucleation) and can induce gas phase (homogeneous) nucleation, resulting in maintenance problems and lower deposition efficiency. In addition, depletion of gaseous reactants also occurs along the reactor requiring complex systems for large substrates.

In a cold wall reactor only the substrate is heated, either inductively or resistively, and the wall of the reactor is cold. Most CVD reactions are endothermic. Therefore, the deposition reaction will occur only on the heated substrate, and negligible deposition occurs on the wall of the reactor. Although these reactors are more complex, they allow greater control over the deposition process, enabling higher quality coatings. However, thermal convection, which occurs in a cold wall reactor, can create concentration gradients of the reactive species and can sometimes result in non-uniform coatings. This can be overcome by performing CVD cold wall deposition at a reduced pressure. Factors that determine the heating method are the size and geometry of the substrate and whether it is conducting or non-conducting. Additionally, by using cold wall CVD and thus avoiding homogeneous nucleation, higher growth rates can be achieved. This drastically reduces the deposition time required to achieve the scintillator coating thickness necessary to absorb most of the incident radiation.

The analysis and optimization of CVD processes requires the application of thermodynamics, chemical kinetics, and mass transport phenomena. An understanding of these parameters allows the user to control the structure, stoichiometry, crystallinity and texture of films [6, 7]. The effects of temperature and supersaturation on growth morphology for a CVD process are known from previous studies. Preferred morphologies for the present invention are platelets and epitaxial growth, while amorphous deposits are to be avoided.

Whether made by PVD or CVD, a scintillator film of the invention is deposited onto a substrate. Suitable substrate materials are preferably smooth, mechanically rigid, largely transparent to x-rays, and either highly reflective or highly transparent to the light emitted by the scintillator. The substrate material should be able to withstand the conditions used for PVD or CVD without significant degradation that would impact film structure or integrity. Examples of suitable substrate materials include, but are not limited to, graphite, quartz, and fiberoptic plate material. The substrate is required for the deposition process, but it can be removed, for example, by mechanically grinding it away, after the film is attached to another structure (e.g., a CCD) at its surface facing away from the substrate.

Figure 20:
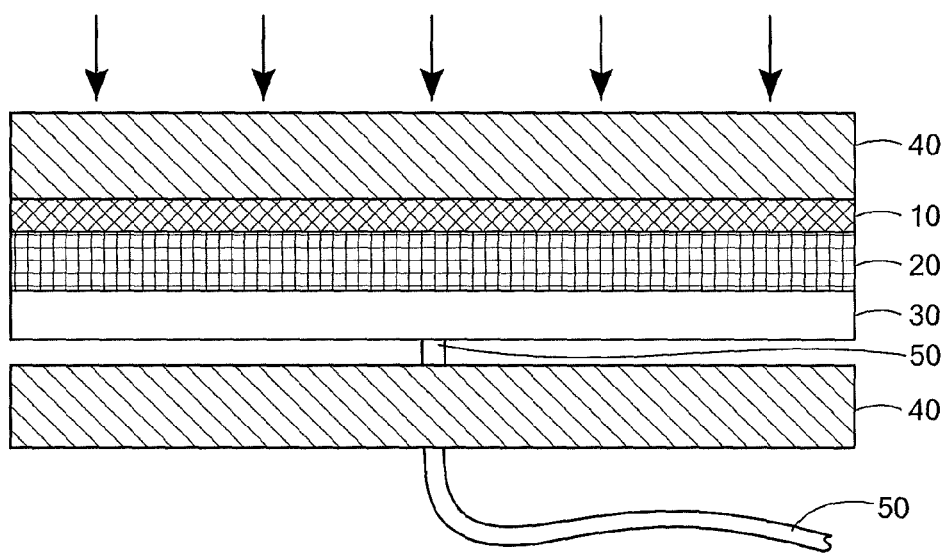
FIG. 20 is a schematic diagram illustrating an embodiment of an x-ray imaging device for dentistry featuring a $Lu_2O_3$:Eu scintillator film according to the invention mounted on a CCD imaging chip.

Scintillator materials containing $Lu_2O_3$:Eu can be incorporated into a variety of devices, particularly optical devices designed to convert x-rays into visible light for quantification or imaging of an x-ray source, or for imaging of an object that scatters or absorbs x-rays. An example of an embodiment suitable for dentistry is shown in FIG. 20. X-rays impinge on the device from the top of the figure (arrows). The scintillator material in the form of film 10 is adhered to a CCD device, shown as layer 20. The thickness of the scintillator will depend on the application; however, the scintillator film should be sufficiently thick to absorb most of the incident x-rays to be imaged or quantified. For example, scintillator layer 10 can be in the range from about 50-500 μm in thickness, preferably about 200 μm thick. The thickness of CCD layer 20 can be, for example, about 350 μm. The CCD layer can be supported by circuit substrate 30. The circuit substrate can be any suitable material, but is preferably a material such as FR4, a glass fiber-epoxy resin material used in printed circuit boards, which is electrically insulating and rigid. Optionally, one or both faces of the device are encased in a layer of housing material 40, such as a plastic material or other material that is transparent to x-rays, at least on the side facing the incoming x-rays. Cable 50 connects the CCD layer to a device such as a computer for input, analysis, display, and storage of signals from the CCD, such as images. Devices containing the $Lu_2O_3$:Eu scintillator material can be used for any purpose related to detection of x-rays by scintillation. For example, such uses include recording dental x-rays; recording any type of medical x-rays such as in mammography, chest x-rays, or diagnostic x-rays; and recording images or performing analysis of any object that scatters or absorbs x-rays, including metals, microelectronics components, and nanomaterials.

The invention contemplates a method of preparing a radiological scintillator coating material by a vapor deposition technique. To make the coating material, a layer of lutetium and europium oxides is deposited onto a substrate by a physical or chemical vapor deposition technique. The ratio of lutetium to europium is selected such that the deposited layer provides effective scintillation in response to incident radiation. The incident radiation is a high energy, short wavelength radiation, such as x-rays. Preferably, the deposited layer is subsequently annealed by heat treatment at a temperature in the range of about 100 to 1400° C., so as to improve the emission characteristics. The invention also contemplates a device for x-ray imaging. Such a device includes the scintillator coating material just described and a semiconductor imaging device. The device can have a configuration such as that shown in FIG. 20, or another configuration suitable for a particular imaging application.

EXAMPLES

Example 1

Physical Vapor Deposition of $Lu_2O_3$:Eu Films

Figure 2:
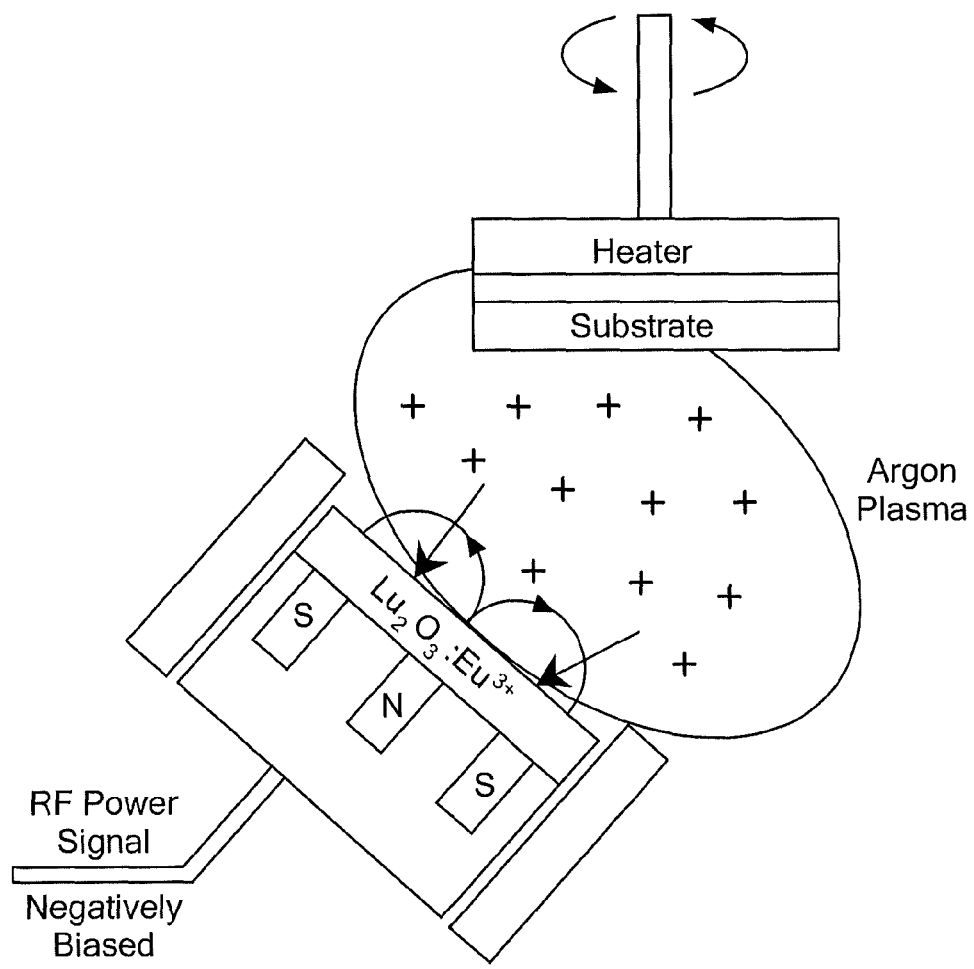
FIG. 2 shows a diagram of a physical vapor deposition (PVD) system using a radio frequency (RF) magnetron sputtering system.

Films of $Lu_2O_3$:Eu$^{3+}$ were successfully deposited using physical vapor deposition (PVD) carried out in a radio frequency (RF) magnetron sputtering device (see FIG. 2). The setup used a 2 inch diameter target angled at 45 degrees with respect to the substrate. The target was made by hot pressing $Lu_2O_3$ powder doped with 5 mol % Eu2O3 at 1700° C. using a graphite uniaxial hot press. A thin 2 inch diameter graphite disc was used as the substrate and it was rotated at approximately 20 rpm to increase uniformity. The RF power source was an Advanced Energy RFX600 capable of producing 600 Watts. Coatings were deposited at 50, 75 and 100 watts and examined. It was determined that 100 watts was the maximum useable power level, above which charging and target damage occurred. The coatings were examined using a Bruker D8 Focus X-ray diffraction (XRD) unit using Cu—Kα radiation to determine orientation, and a Zeiss field emission scanning electron microscope (SEM) to examine the microstructure.

Figure 3:
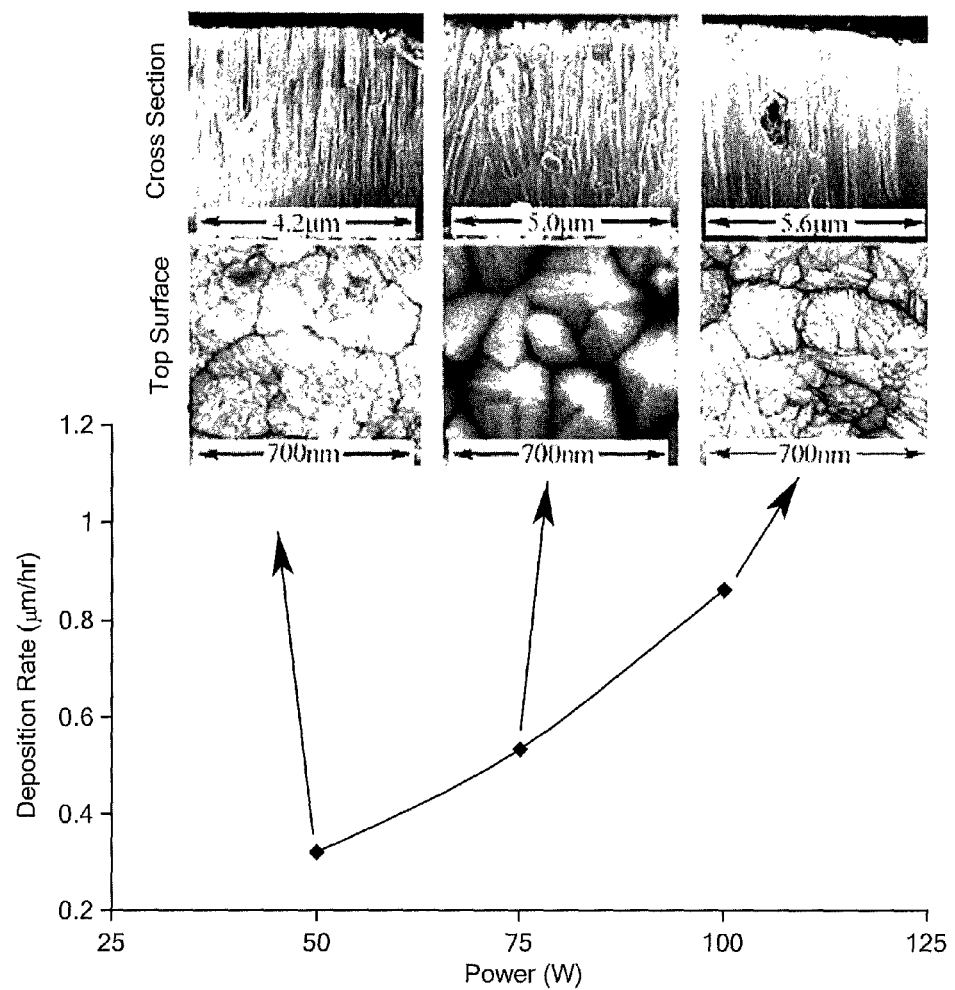
FIG. 3 shows the effect of RF power on deposition rate of $Lu_2O_3$:Eu by a PVD process. Morphology of the material is shown above each condition by scanning electron microscopy (SEM) in cross section and top view.
Figure 4:
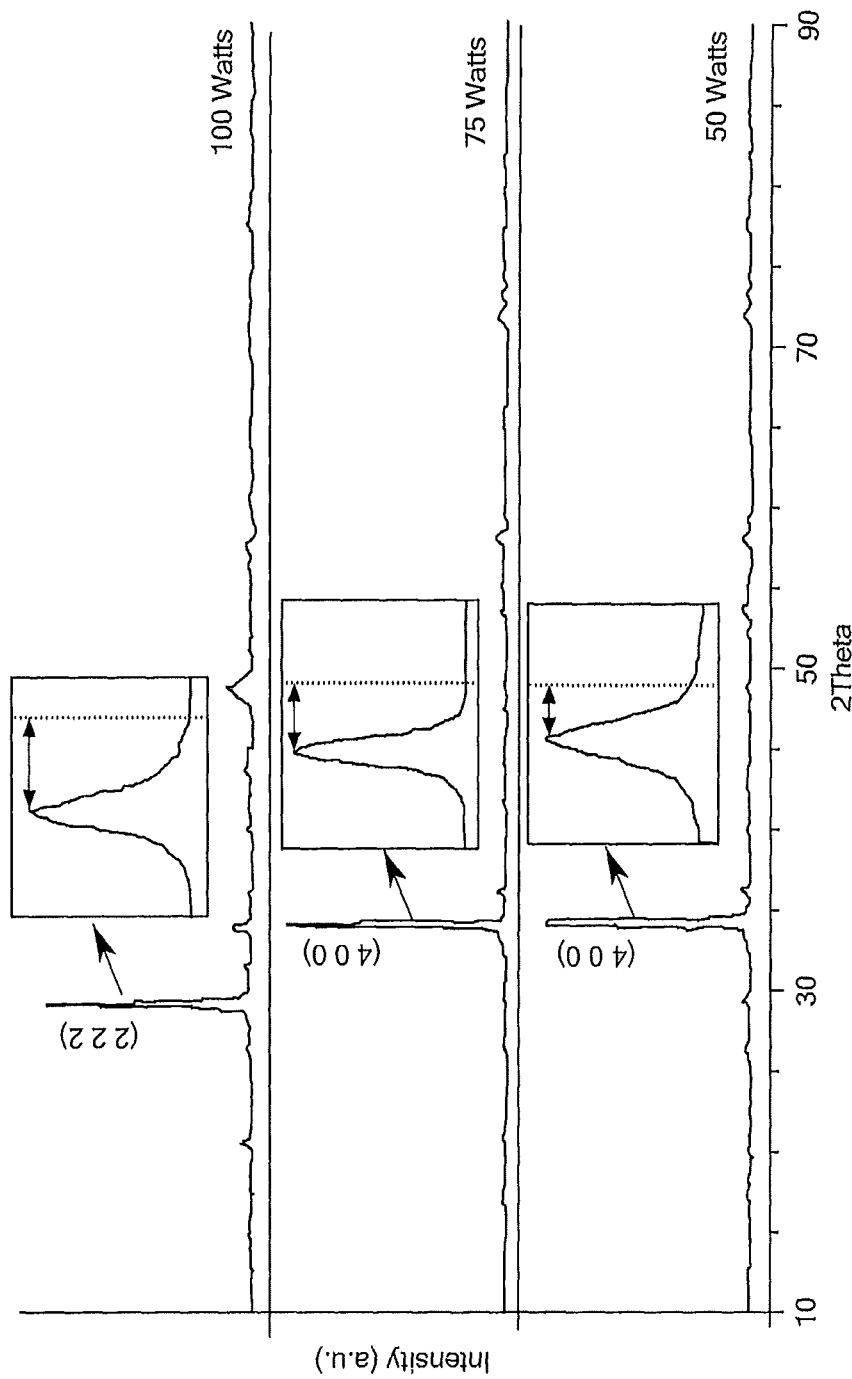
FIG. 4 shows the results of x-ray diffraction analysis on $Lu_2O_3$:Eu deposited by a PVD process at room temperature for different RF power settings (50, 75, and 100 watts).

Microstructural analysis of the top surface and the fractured cross sections, as shown in FIG. 3, revealed that growth morphology depended on input power. The surface images showed a clear transition from what appears to be cellular growth to plate growth. At 50 W and 100 W the columnar growth appeared to be of uniform width and perpendicular to the surface, whereas at 75 W, the columnar growth became radial. The diameter of the columnar growth is not clear from the fractured cross section. However, top surface images shown in FIG. 3 clearly show larger boundaries, indicative of columnar grain growth. Grain diameter measurements indicated a trend of decreasing columnar diameter with increasing power (or deposition rate) as shown in Table 1. The columnar growth was determined to be (100) textured for low input power and (111) textured for high input power as determined from the XRD pattern (FIG. 4). It is noteworthy that the intensities of the (100) and (111) peaks were low, indicating that crystallinity/orientation was not significant. Low intensity diffraction peaks from other planes further suggest that not all growths were perpendicular and growth was slightly polycrystalline. This is most likely a result of slow kinetics, because the low thermal energy did not enable the newly formed grains to grow epitaxially. Furthermore, the XRD patterns were increasingly shifted towards a larger unit cell with increasing power, which is typically attributed to growth stresses. The (100) orientation is a lower energy growth direction, and with sufficient stresses it can shift towards (111) growth.

TABLE I

X-ray diffraction analysis compared with SEM grain size measurements

| Power (Watts) | Measured Grain Size (nm) | Lattice Distortion | Volume Distortion |
|---|---|---|---|
| 50 | 415 | 1.0% | 3.0% |
| 75 | 290 | 1.2% | 3.6% |
| 100 | 247 | 2.1% | 6.3% |

In a PVD sputtering system, the plasma intensity is dependent on the power applied, which also affects the sputtering rate. The plasma itself can attain high temperatures and can provide some thermal energy to the coating, and the substrate can reach temperatures up to 100° C. However, the plasma provides a relatively large amount of thermal energy to a very thin layer, notably the deposition layer. This is believed to be the reason for the drastic change in coating morphology observed at 75 W. At this power there is a balance between deposition rate and thermal energy provided by the plasma that enables better crystallization. At 50 W the low intensity plasma provides low thermal energy and, despite reduced deposition rates, is not adequate for crystalline growth. At 100 W, despite increased plasma thermal energy, the atoms did not have sufficient time to rearrange because of the higher density of incoming atoms.

Example 2

PVD Films Deposited on Heated Substrates

Figure 5A:
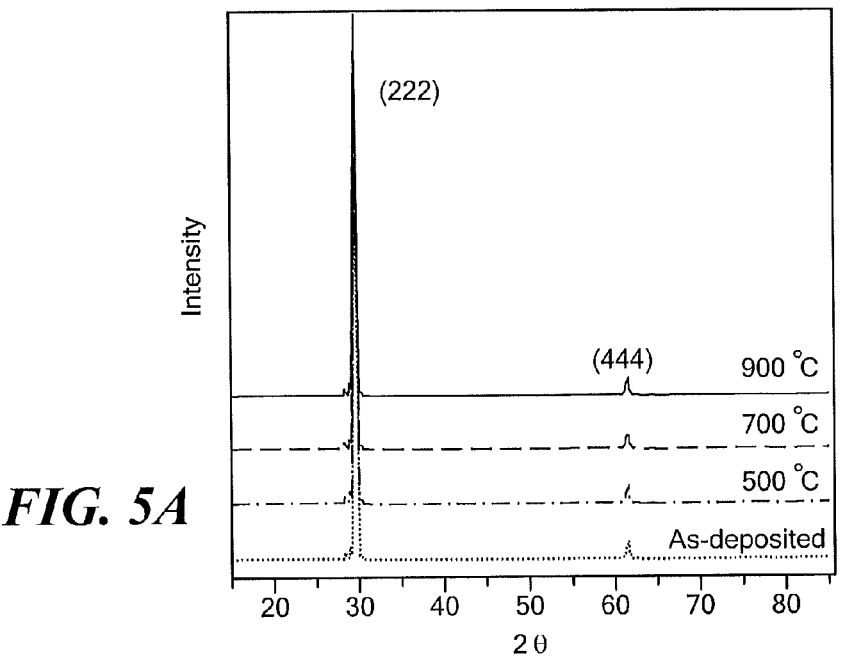
FIG. 5A shows the results of x-ray diffraction analysis of $Lu_2O_3$:Eu deposited by PVD at 400° C. and treated subsequently at the indicated temperatures.
Figure 5B:
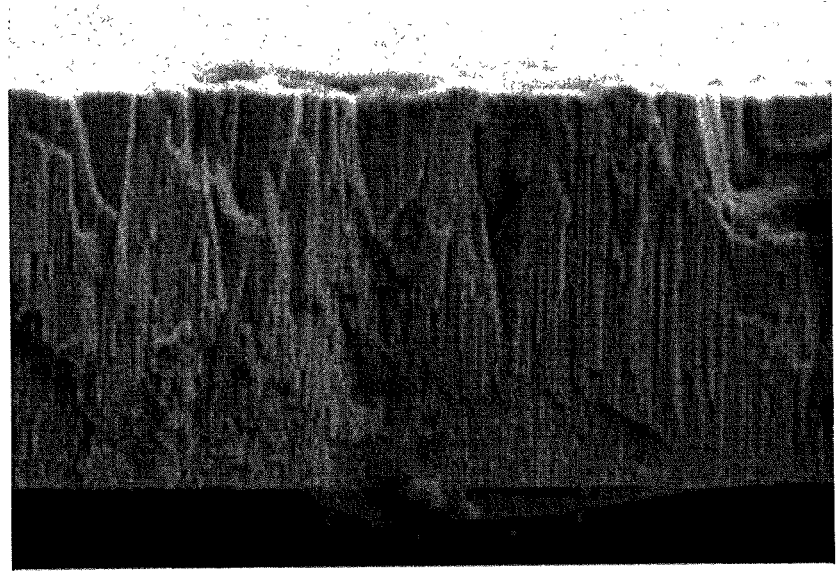
FIGS. 5B and 5C show morphology by SEM of the 400° C. material as deposited.
Figure 5C:
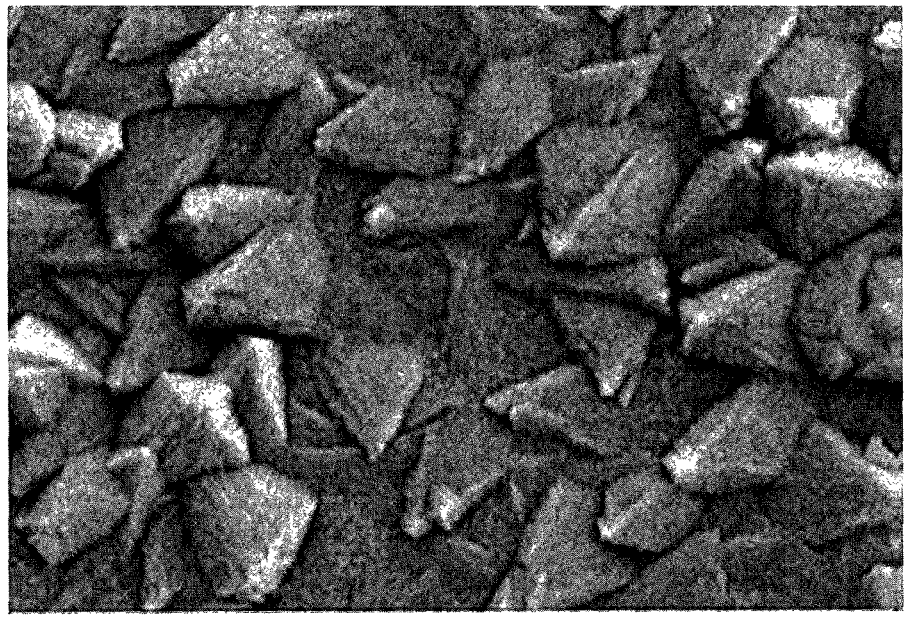

Deposition by PVD at a substrate temperature of 400° C. resulted in a coating that exhibits a significantly higher degree of orientation than that obtained at room temperature. FIG. 5A shows a plot of the XRD data for films deposited at increasing substrate temperature. The peaks remain slightly shifted toward higher unit cell dimensions, indicating some residual stress and suggesting the need for even greater thermal energy, perhaps by heating to 700-900° C. The micrograph of these fracture cross-sections (FIG. 5B) reveals a columnar structure, and the corresponding surface micrograph (FIG. 5C) contains randomly oriented pyramidal shapes similar to the 75 W coating in FIG. 3, suggesting that heated substrates accommodate higher material fluxes than they would otherwise tolerate at room temperature.

Example 3

Effect of Heat Treatment on $Lu_2O_3$:Eu Films Deposited by PVD

Figure 17A:
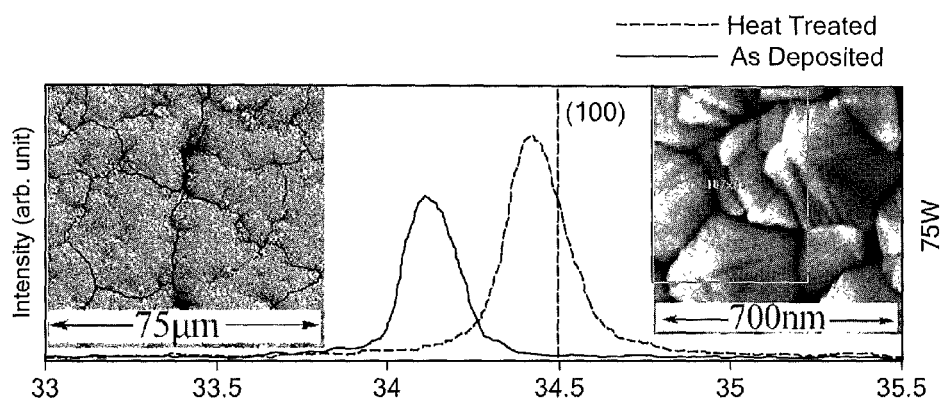
FIGS. 17A and 17B show x-ray diffraction analysis and morphology by SEM of heat treated (900° C., 2 hours) $Lu_2O_3$:Eu deposited by PVD at the indicated RF power settings (75 watts for FIG. 17A, 50 watts for FIG. 17B). The (100) peak is shown for the as deposited material for comparison.
Figure 17B:
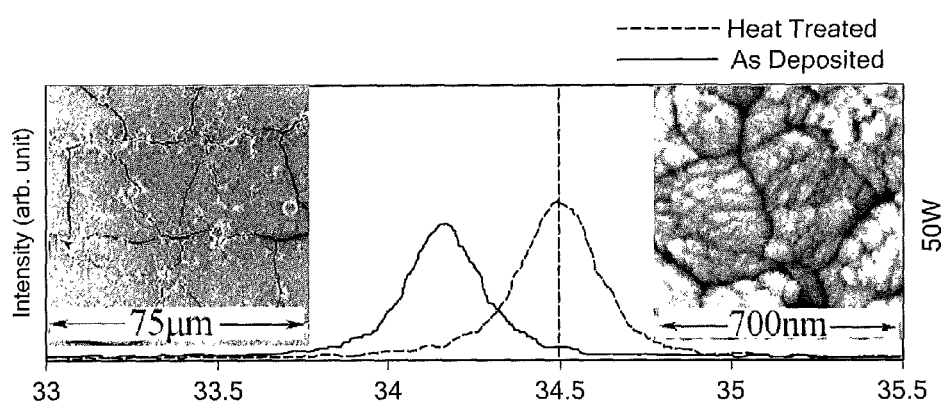

To study the effects of annealing by heat treatment, coatings were post-treated in a tungsten furnace at 900° C. in an argon atmosphere for 2 hours. The samples from Example 1 were heat treated to increase crystallinity and observe changes in morphology. As seen in FIG. 17, the (100) peak reverted back to the theoretical position after heat treatment, indicating stress relief. However, associated with the restored unit cell is a subsequent volume change resulting in reduced thickness and cracking (FIG. 17). In the 100 W case, the volume distortion led to loss of adhesion, making further analysis on the heat treated sample almost impossible. One can observe in FIG. 17 that the morphology of the coating remained identical to the as-deposited coating, indicating stability of the coating. A small increase in the intensity of the (100) peak was observed, indicating slight grain growth or increase in crystallinity. In FIG. 18C it can be seen that the edge of the 100 W sample remained adherent, which can be attributed to the non-uniformity of deposition conditions. These films were deposited on a graphite substrate, and adhesion might be different with another substrate material. In magnetron sputtering, a ring source is created, which in the present case was angled at approximately 45 degrees to a rotating substrate. The angling and rotation was used to improve thickness uniformity, but resulted in non-uniform plasma heating and deposition angles, which are critical growth factors. Furthermore, the kinetic energy of the ejected material plays a crucial role in the coating properties and is a function of the travel distance and total pressure. Therefore, the center of the substrate was exposed to relatively constant deposition conditions, while the outer edges varied significantly every half rotation. The XRD pattern of the outer edge was that of a partially polycrystalline coating.

One of the indicators of the extent of crystallization in a scintillating material is the emission intensity and spectrum. The emission spectrum of the as deposited and heat treated samples were measured using cathodoluminescence. The emission intensity for the as deposited sample was found to be too low to be detected, while the heat-treated samples had a standard emission spectrum. Ultraviolet light at 254 nm also induces emission due to the charge transfer band at approximately 250 nm in the host material, as seen in FIG. 18A-18C. The lack of emission by the as deposited samples can be attributed to either low crystallinity or a large number of defects which act as charge traps resulting in non-radiative transitions. Once heat-treated, however, the defects were mostly eliminated, and increased crystallinity resulted in improved emission. The 75 W sample (FIG. 18B) produced the highest emission intensity.

In summary, the as-deposited coatings were partially crystalline and did not scintillate. However, thermal treatment of the coatings resulted in increased crystallinity and fewer defects, leading to excellent scintillation properties.

Example 4

Chemical Vapor Deposition of $Lu_2O_3$:Eu Films

Many CVD processes use the metal chloride-$H_2$—$CO_2$ system [6-7]. In this study, thermodynamic calculations using HSC chemistry simulation software (see www.hsc-chemistry.net) were used to determine the viability of the CVD process. The hypothesized deposition reaction equation for $Lu_2O_3$:$Eu^{3+}$ as shown in Eq. (1) was made using a combination of Eqs. (2) and (3).

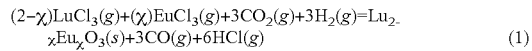

(1)

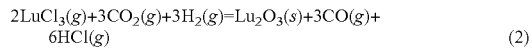

(2)

$\Delta G_{rxn,2}$=-439 kJ/mol of $Lu_2O_3$, 1000° C.

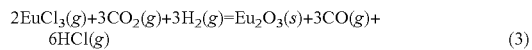

(3)

The Gibbs free energy of reaction for Eq. (2) is –439 kJ/mol as opposed to a value of –170 kJ/mol for Eq. (3) at 1000° C. Although this difference in free energy could result in a variance between deposit and gas composition, it was favorable in this study, as low amounts of Eu are desired in the coating deposits. Even though $LuCl_3$ and $EuCl_3$ are solids at room temperature, their vapor pressure at deposition temperatures (1000° C.) are high enough to provide an adequate reactant flow. Since the chlorides are extremely hygroscopic, they were generated in situ by reacting lutetium and europium metal with judicious control of the temperature and the chlorine flow rates. It is known that a europium concentration of 5-7 mol % in the $Lu_2O_3$:$Eu^{3+}$ system yields the highest emission intensity [8, 9]. Furthermore, the ability to interpret an image is directly related to the emission intensity uniformity, and thus dopant uniformity is essential to the imaging process. With knowledge of the variance in free energy of formation of $Lu_2O_3$ and $Eu_2O_3$, the ratio of Lu and Eu in the internal chloride generator was empirically determined in order to achieve the desired level of Eu doping. To maintain 5-7 mol % Eu in the deposit, both metals were uniformly mixed to avoid excess preferential reactions. Europium chloride melts above 730° C., and although lutetium chloride melts at 925° C., it sublimates above 750° C. By combining elevated temperature and low pressure, it is possible to ensure that the metal-chlorine reaction is the limiting kinetics and not the evaporation/sublimation rate, thus providing the necessary control.

Figure 6:
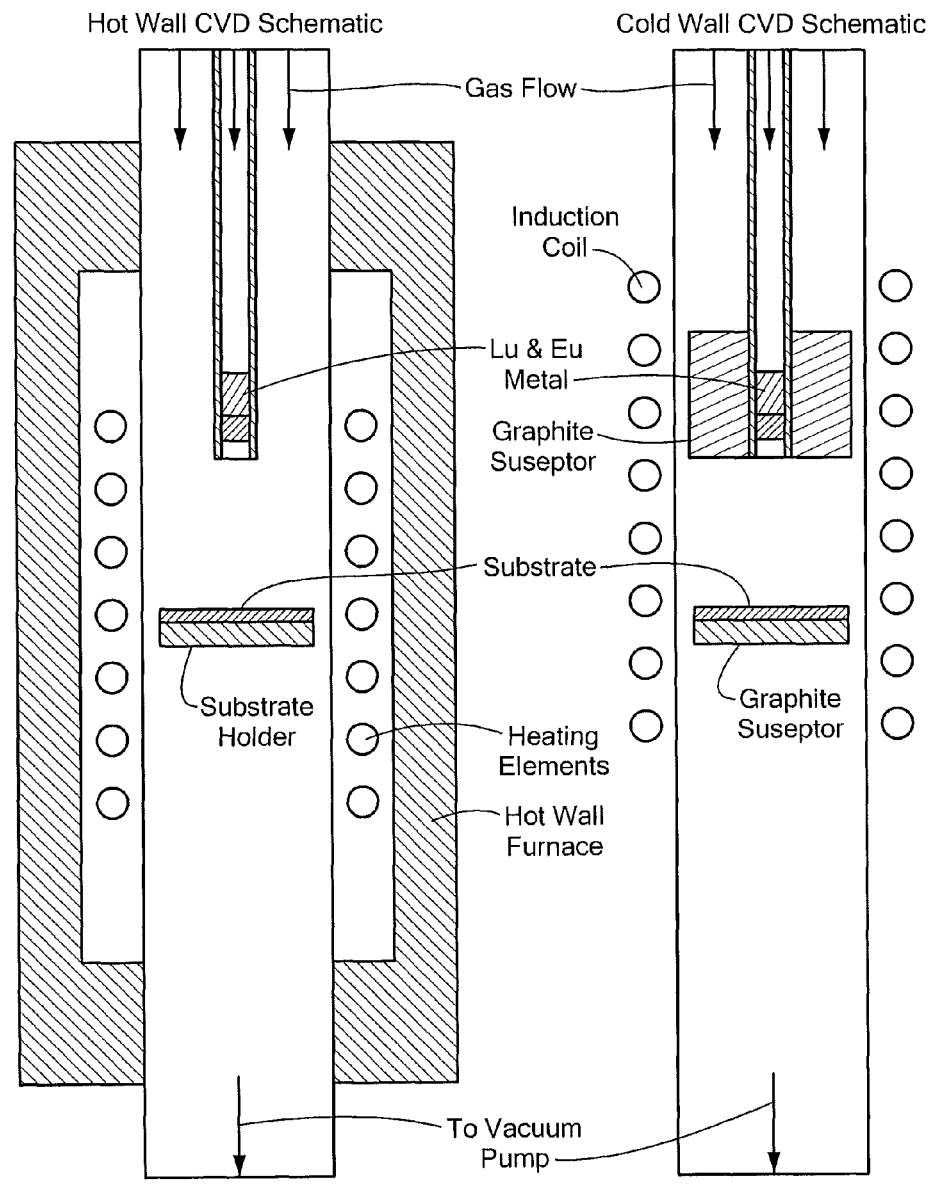
FIG. 6 shows a diagram of cold wall and hot wall chemical vapor deposition (CVD) reactors that can be used to deposit $Lu_2O_3$:Eu according to the invention.
Figure 7A:
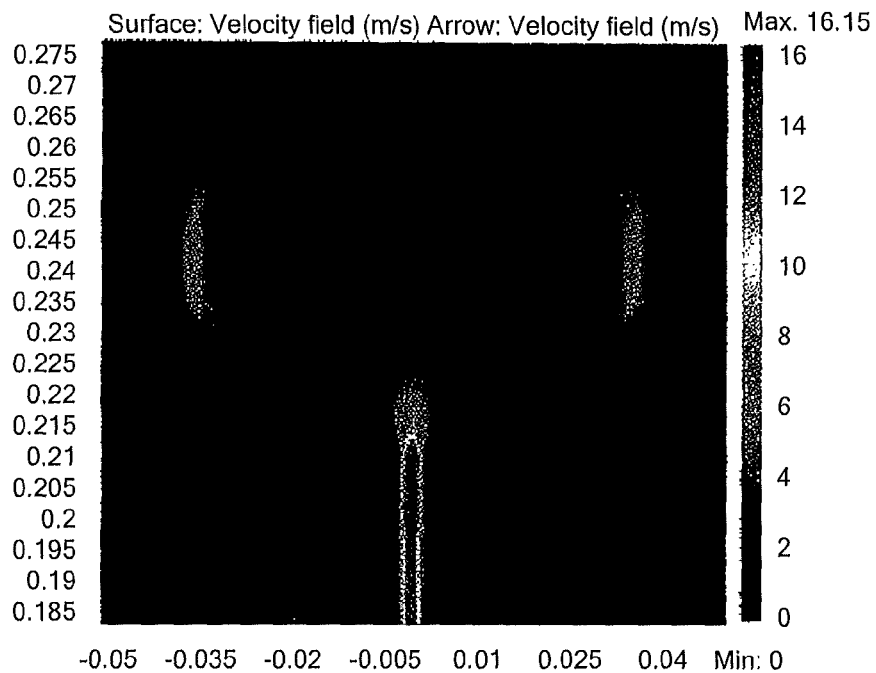
FIGS. 7A-7D show the results of Femlab modeling of CVD flow dynamics (7A and 7C) and temperature profiles (7B and 7D) for two different separation distances between the crucible and substrate (1.25" for 7A and 7B, 3" for 7C and 7D).
Figure 7B:
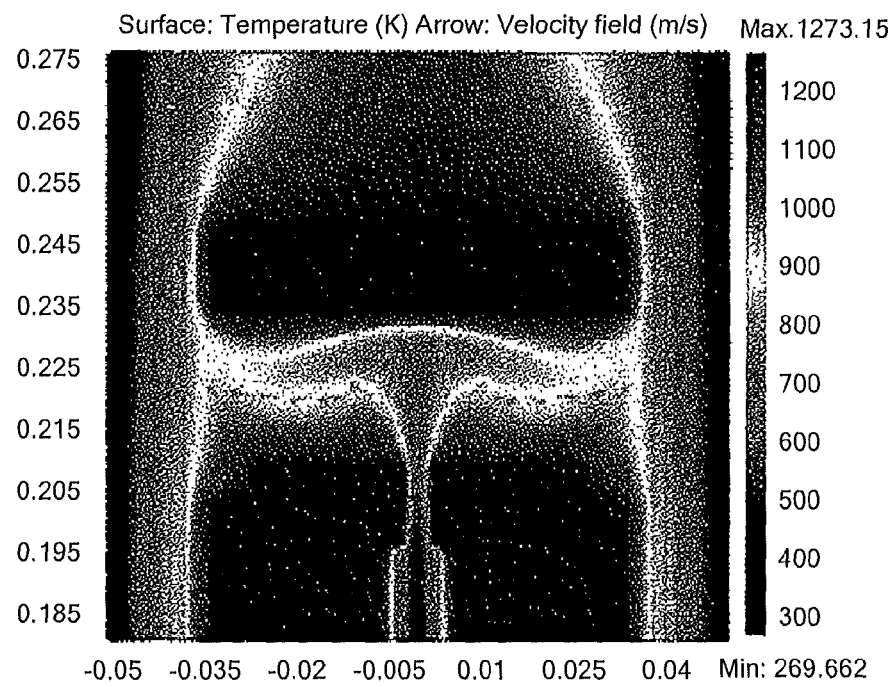
Figure 7C:
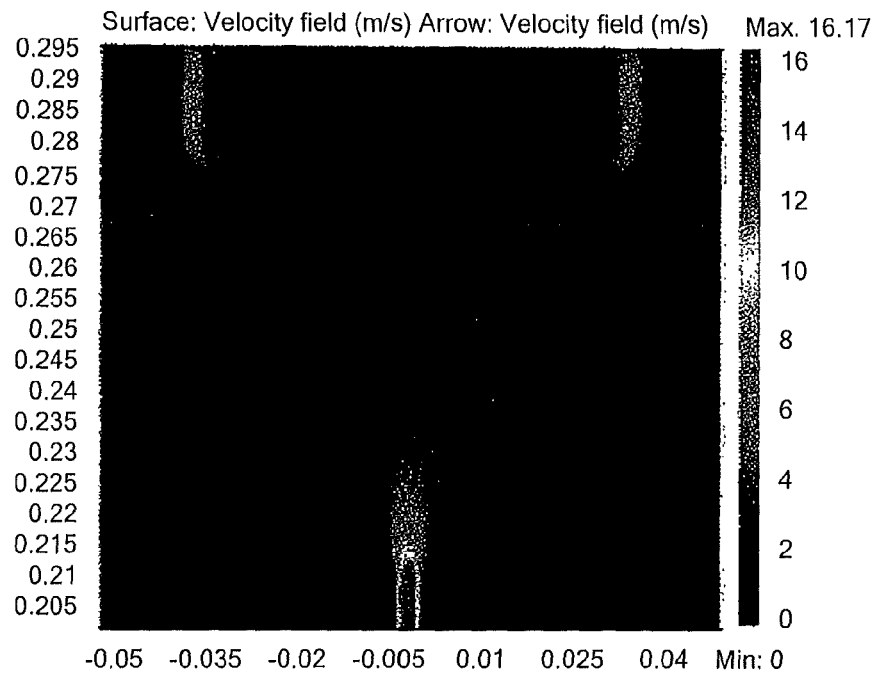
Figure 7D:
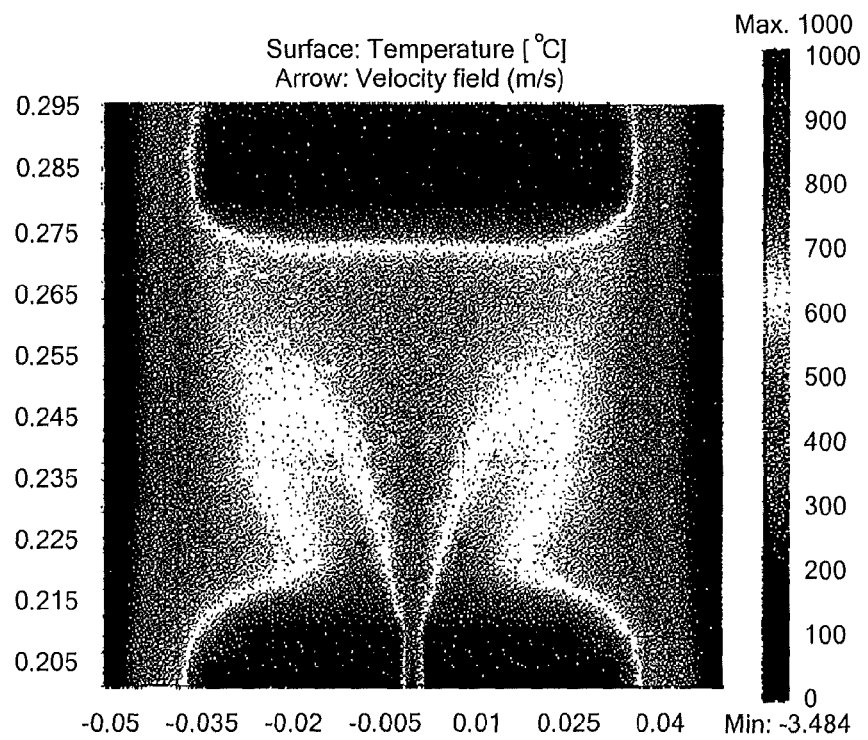

The cold wall CVD reactor used an RF induction heater to heat the substrate and crucible using graphite susceptors (see FIG. 6). The reactants used for deposition were the metal chlorides ($LuCl_3$ and $EuCl_3$), $CO_2$, $H_2$ and Ar as diluant. Excess $H_2$ was present to ensure complete reduction of metal chlorides. Process parameters ranged from 950° C. to 1050° C. for both the substrate and the generator, between 50 and 150 mbar, and a total flow rate of approximately 2 slm. Morphological analysis of the coatings was performed using a Zeiss VP40 high resolution scanning electron microscope (SEM) in conjunction with a Bruker D8 Focus X-ray diffractometer (XRD) in θ/2θ mode. Emission properties were confirmed using a Gatan MonoCL2 cathodoluminescence spectrometer.

Since many parameters affect the coating structure and properties, various configurations were designed and tested. One of the problems encountered was the formation of metal oxy-chlorides due to a high metal chloride partial pressure and short mixing times. This was resolved by maintaining a minimal distance (e.g., 60 mm or greater, depending on the reactor) between the substrate and the gas outlet to allow for proper mixing and by supplying sufficient $CO_2$ and $H_2$ to fully reduce the metal chlorides.

Two of the key features in a CVD process are the fluid dynamics and temperature profile of the gases as they approach the substrate. The gas velocity and profile is determined by the total gas flow rate and the outlet design. The temperature profile is determined by the crucible and substrate temperature, and the fluid dynamics. The way the gases pass through the crucible and the flow rate are determining factors in the amount of thermal energy gained prior to mixing and determines the temperature profile of the approaching gas. Modeling was performed using the Comsol multiphysics modeling software Femlab to obtain a basic insight into the process. The simulated flow dynamics and temperature profiles are shown in FIG. 7A-D. This analysis is specific for the CVD reactor used and would have to be modified for a different reactor. The modeling showed a clear relationship between the crucible temperature, substrate temperature, total flow rate, and temperature profile.

Further parameters were generally as follows. The amount of lutetium metal was about 0.8 g and europium metal about 0.1 g. The vacuum was 75 Torr. The flow rates were 6 sccm for $Cl_2$, 800 sccm for Ar, 312 sccm for $CO_2$, and 1250 sccm for $H_2$. Crucible temperature was 950° C. for sublimation of $LuCl_3$ and $EuCl_3$, and the substrate temperature was 1050° C.

This set-up configuration led to the deposition of coatings in a columnar fashion with a strong orientation preference growth directly from the first nucleated, equitaxial layer deposited on the substrate. Such microstructure is a result of high supersaturation and limited lateral diffusion. This structure is desirable for radiation detection since every column would act as one 'pixel'.

When grown at approximately 1000° C. on an amorphous quartz substrate with a growth rate of approximately 3.2 μm/hr, a columnar structure emerged as seen in FIGS. 9A and 11B. The columnar grains appear to have an average diameter of approximately 1.5 μm and a total coating thickness of approximately 6.4 μm. When comparing the XRD plot in FIG. 10A to a polycrystalline powder diffraction plot in FIG. 10B, a clear (100) orientation preference is visible. Such a preference for the (100) orientation indicates a free energy minimization for growth in this direction. Observations of the surface morphology in FIG. 9B revealed the columnar growth to consist of stacked platelets or discs growing perpendicular to the (100) direction. Such a layer to layer formation has been defined as Frank-van der Merwe (FM) growth and typically leads to smooth surfaces.

Growth conditions were then modified by decreasing the ratio of metal chloride to unreacted chlorine while keeping the total chlorine flow rate constant. This led to the deposition of a highly facetted columnar structure, as seen in FIG. 11, with a growth rate of 0.5 μm/hr and a coating thickness of approximately 2.4 μm. The columnar growth appears to be single grained, with an average diameter of approximately 450 nm and with a clear surface morphology. This could be indicative of either a cellular or dendritic growth or simply a surface effect. This type of growth has been referred to Volmer-Weber (VW) and typically leads to rough surfaces. The XRD plot in FIG. 12 combined with the SEM images in FIGS. 11A and 11B shows the preferred orientation to be in the (100) direction, perpendicular to the substrate surface. The ability to drastically tailor morphology, and size of the columnar grains via CVD processing parameters can be beneficially used to engineer coatings to fit specific applications.

Figure 13:
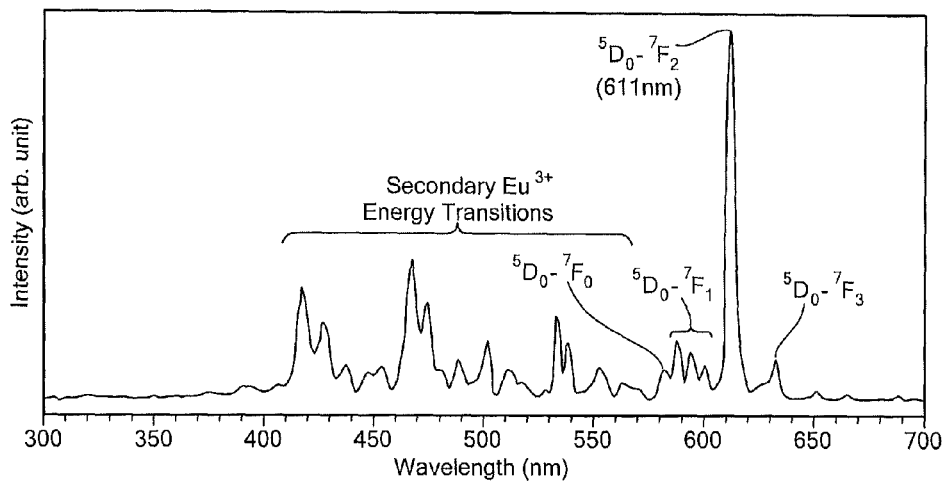
FIG. 13 shows a cathodoluminescence spectrum of highly faceted columnar $Lu_2O_3$:Eu deposited by CVD.

Both lutetium and europium oxide have similar body centered cubic (BCC) lattice structure ($Lu_2O_3$=10.39 Å, $Eu_2O_3$=10.87 Å) and form a complete solid solution. For optimal emission to occur, europium must form a solid solution by substituting into the lutetium site of $Lu_2O_3$ as $Eu^{3+}$. Although lutetium has only one stable oxidation state of +3, meaning it can only exist as $Lu_2O_3$, europium can have either +2 or +3 as its oxidation state, creating structures such as $EuO$, $Eu_2O_3$, and $Eu_3O_4$ or potentially more. Thermodynamically, $Eu_2O_3$ is significantly more favorable; however, it is possible to deposit non-equilibrium phases in CVD. Experimental results confirmed this possibility when solely depositing europium yielded europium monoxide (EuO). It was hypothesized that as a result of the co-deposition, the europium would be forced into the +3 valence. Furthermore, it is possible for europium oxide to form a second phase rather than go into solution which would result in non-optimal emission. This was visible in certain circumstances where a second phase of $Eu_2O_3$ was visible in the XRD plots, proving the formation of a solid solution to be difficult. However, XRD plot in FIG. 12 shows no second phase, and the emission spectrum in FIG. 13 confirmed europium to be in the correct valence, proving that a solid solution has been achieved. If $Eu^{2+}$ were present, there would be a broad emission peak from 400 nm to 500 nm; however, only $Eu^{3+}$ is visible, which has many peaks and the standard maximum intensity peak at 611 nm, which corresponds to the $^5D_0$-$^7F_2$ transition.

Example 5

Effect of $CO_2$ Partial Pressure on CVD

Figure 8A:
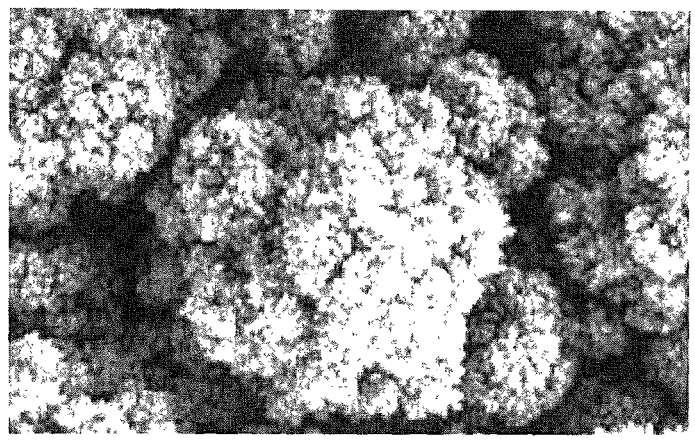
FIGS. 8A-8C show the morphology by SEM of CVD films of $Lu_2O_3$:Eu deposited at substrate temperature of 950° C. and $CO_2$ flow of 300 sccm (FIG. 8A), 1000° C. and $CO_2$ flow of 400 sccm (FIG. 8B), and 1050° C. and $CO_2$ flow of 500 sccm (FIG. 8C).
Figure 8B:
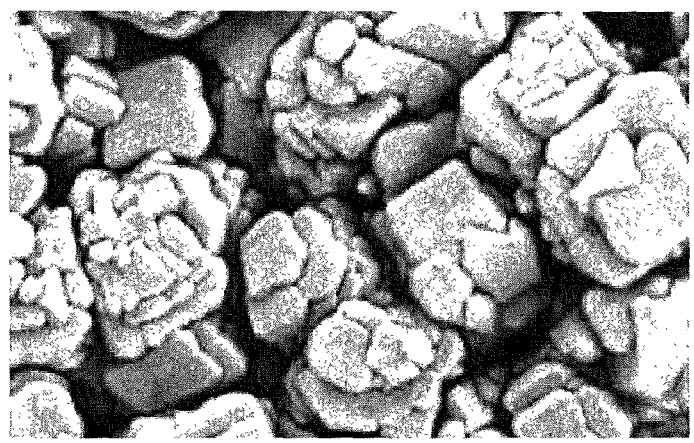
Figure 8C:
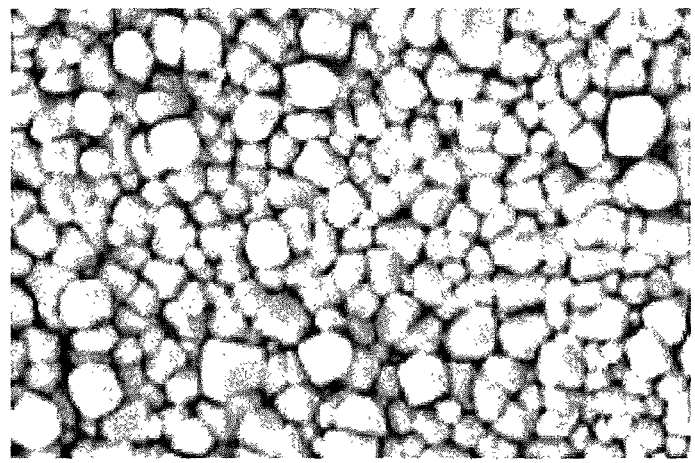

A series of CVD experiments on amorphous quartz substrates, with a crucible-to-substrate separation of 1.25" indicated that varying deposition conditions produce a wide range of coating morphologies, as shown in FIG. 8. One particularly sensitive parameter was the $CO_2$ partial pressure, in which small changes drastically affected the growth mechanism. At low temperature and low $CO_2$ partial pressure, the deposition did not show any evidence of a preferred orientation (FIG. 8A). However, as the temperature was increased, the grain size increased due to increased diffusion and, counter-intuitively, the growth rate decreased. In this case, no homogeneous deposition occurred, suggesting that there is a decrease in the deposition driving force or a depletion of reactants prior to deposition. Upon increasing the $CO_2$ partial pressure, there was a sudden change in the growth mechanism, resulting in the formation of stacked platelets or discs growing preferentially in the <100> direction, as shown in FIG. 8B. This was confirmed by XRD measurements, as shown in FIG. 10A.

Example 6

Emission Properties of Europium-Doped Lutetium Oxide Films

Figure 14A:
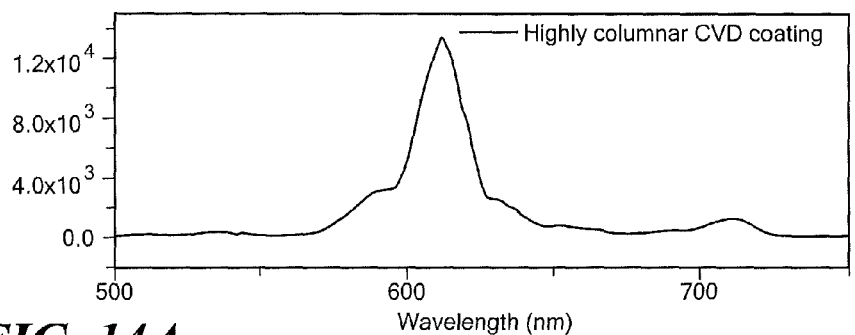
FIGS. 14A and 14B show radioluminescence emission spectra for Eu-activated $Lu_2O_3$ for a CVD film (FIG. 14A) and a hot-pressed ceramic film (FIG. 14B).
Figure 14B:
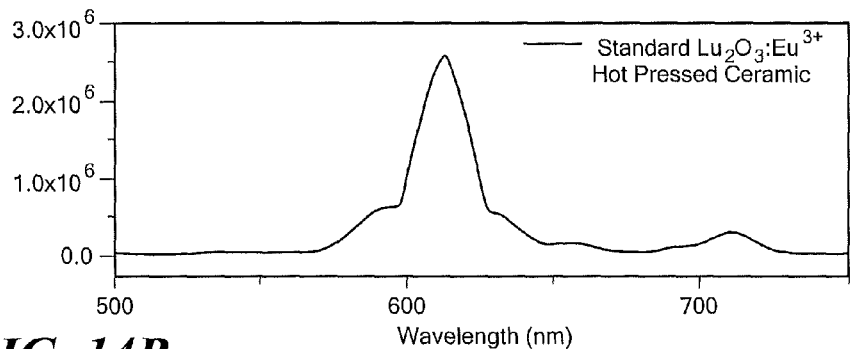

In contrast to the significant differences in morphology of $Lu_2O_3$:Eu films as described above, their spectroscopic profile is relatively less sensitive to the conditions of deposition. This is largely due to the fact that the emitted light is generated by optical transitions between states of the 4f electronic shell, which is well shielded from environmental influences by the surrounding 5d shell. The effect is exemplified in FIG. 14, where no perceptible difference in shape was found between the radioluminescence emission spectra of $Lu_2O_3$:Eu in the form of a CVD film (FIG. 14A) and a standard hot pressed ceramic (FIG. 14B). The radiative decay time, at about 1 ms, was similarly unaffected.

Figure 15:
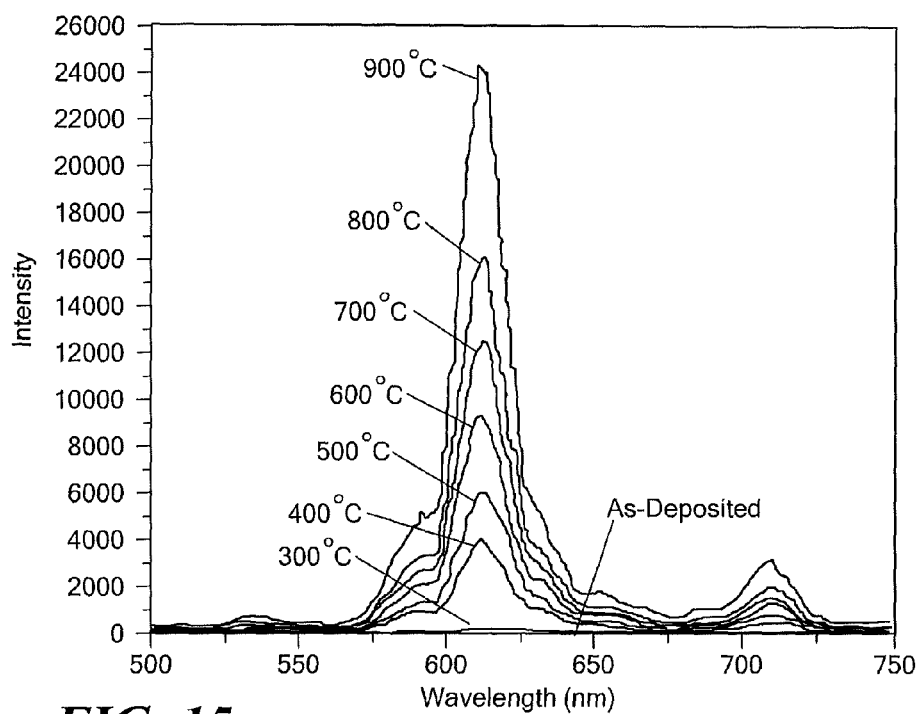
FIG. 15 shows radioluminescence emission spectra of [CVD???] deposited $Lu_2O_3$:Eu films that were annealed at the indicated temperatures after deposition. Peak emission is a monotonically increasing function of the temperature (highest value at 900° C. annealing temperature).

While the spectral shape was not significantly altered by fabrication conditions, the emission intensity most decidedly was. This is because the excitation energy deposited into the host lattice by the ionizing radiation must travel a substantial distance through that lattice (as mobile electrons, holes, and excitons) before it can actually reach an emitting center. This process is quite vulnerable to the malign influence of lattice defects, which degrade both the speed and efficiency of the energy transport. It can be seen from FIG. 15 that a simple post-deposition annealing treatment had a profound effect on the efficiency of the scintillation from a deposited $Lu_2O_3$:Eu film, causing a monotonic increase in emission with annealing temperature. The increase in light emission for post-deposition heat treatment was about two orders of magnitude for heat treatments over the range from 300° C. to 900° C.

Example 7

Imaging Properties of Europium-Doped Lutetium Oxide Films

Figure 16:
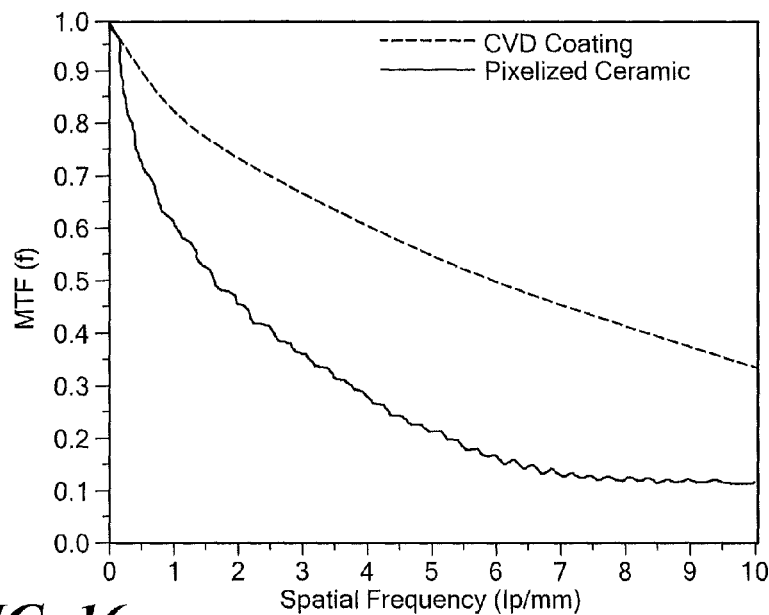
FIG. 16 shows the modulation transfer function (MTF) value of a $Lu_2O_3$:Eu coating deposited by CVD (upper curve) compared to the published values for a pixelated ceramic (lower curve, from [5]).

In order to demonstrate the imaging performance of a $Lu_2O_3$:Eu film according to the invention, the modulation transfer function (MTF) of a graphite-deposited PVD film was measured. The MTF is a measure of the contrast in an image of black and white line pairs as a function of their spatial frequency, and provides a quantifiable value representing the ability to distinguish small features as they become smaller and smaller. In FIG. 16, the MTF curve for a CVD coating according to the present invention is compared with the MTF curve for a pixelated ceramic, as reported in the literature [5]. It is clear that the coating of the present invention has an extremely good MTF curve, which is markedly superior to that of the conventional ceramic.

Figure 19:
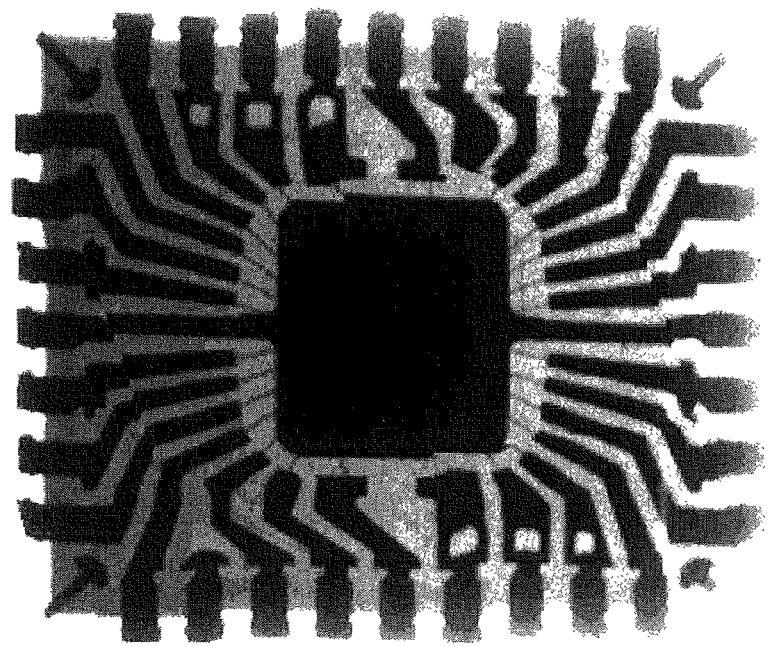
FIG. 19 shows an x-ray image of an integrated circuit chip recorded using radioluminescence from a $Lu_2O_3$:Eu coating according to the invention [PVD or CVD?] glued to a CCD camera.

A radiographic (x-ray) image of an integrated circuit chip was obtained using a PVD scintillator coating according to the present invention mounted on a CCD chip, in an arrangement as shown in FIG. 20. The image so obtained is shown in FIG. 19. The image demonstrates very good contrast and dynamic range, and 25 μm bond wires in the integrated circuit are clearly seen in the image. The image was acquired using a mammography X-ray source operated at 28 kVp, 160 mAs, with the source to specimen distance set at 66 cm.

While the present invention has been described in conjunction with certain preferred embodiments, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

REFERENCES

1. I. Shestakova, V. Gaysinskiy, J. Antal, L. Bobek and V. V. Nagarkar, Nucl. Instr. and Meth. In Phys. Res. B 263, 234 (2007).
2. E. Zych, J. Phys. Condens. Matter 14, 5637 (2002).
3. Pierson, H. O. Handbook of Chemical Vapor Deposition. Noyes, Park Ridge, N. J. (1992).
4. Bunshah, R. F., et al., Deposition Technologies for Films and Coatings, Development and Applications, Materials Sciences Series, ed. Bunshah R. F., Noyes, Park Ridge, N.J. (1982).
5. Farman, T. T., et al., Oral Surg., Oral Med., Oral Pathol., Oral Radiol., & Endodontics 99:608-613 (2005).
6. Pierson, H. O., Handbook of Chemical Vapor Deposition. Noyes, Park Ridge, N.J. (1992).
7. Hitchman, M. L., Jensen, K. F., Eds., CVD Principles and Applications, San Diego Academic Press, London (1993).
8. Tojan-Piegza, J., et al., Comparison Of Spectroscopic Properties Of Nanoparticulate Lu2O3:Eu Synthesized Using Different Techniques, J. Alloy Compd. 308:123-9 (2008).
9. Lempicki, A. et al., A New Lutetia-Based Ceramic Scintillator For X-Ray Imaging, Nucl. Instrum. Meth. A 488: 579-90 (2002).

What is claimed is:

1. A method of preparing a radiological scintillator coating material by vapor deposition, the method comprising depositing a layer of $Lu_2O_3$ and $Eu_2O_3$ onto a substrate by vapor deposition, the layer having a preferentially oriented grain structure.

2. The method of claim 1, wherein the vapor deposition method comprises the steps of:
    (a) providing a target comprising a compressed powder consisting essentially of from about 85 to 95 mol % $Lu_2O_3$ and from about 5 to 15 mol % $Eu_2O_3$ and a substrate to be coated with the scintillator coating material; and
    (b) subjecting the target to physical vapor deposition to release material from the target and deposit the material as a scintillator coating comprising $Lu_2O_3$ and $Eu_2O_3$ onto the substrate.

3. The method of claim 2, wherein the vapor deposition comprises plasma sputtering in a radio frequency magnetron sputtering system.

4. The method of claim 3, wherein the plasma comprises argon.

5. The method of claim 4, wherein the plasma comprises less than 1% oxygen.

6. The method of claim 3, wherein the pressure of the sputtering system is from about 0.5 to 20 mTorr.

7. The method of claim 3, wherein the radio frequency power of the magnetron sputtering system is from about 16 to about 32 watts per square inch of target area.

8. The method of claim 3, wherein the substrate is heated during sputtering to a temperature from about 100 to 1000° C.

9. The method of claim 1, wherein the substrate is a fiber optic plate.

10. The method of claim 1 resulting in preferentially oriented columnar grain growth of the scintillator coating.

11. The method of claim 1, further comprising the step of:
    (c) annealing the scintillator coating by heat treatment at a temperature in the range of about 100 to 1400° C.

12. A non-pixelated radiological scintillator coating material comprising about 85 to 95 mol % $Lu_2O_3$ and about 5 to 15 mol % $Eu_2O_3$ having a preferentially oriented columnar grain growth structure.

13. The scintillator coating material of claim 12 comprising 95 mol % $Lu_2O_3$ and 5% $Eu_2O_3$.

14. The scintillator coating material of claim 12 made by a physical vapor deposition technique or a chemical vapor deposition technique.

15. A method of preparing a radiological scintillator coating material by vapor deposition, the method comprising depositing a layer of lutetium and europium oxides onto a substrate by a physical or chemical vapor deposition technique, whereby the layer provides effective scintillation in response to incident radiation.

16. The method of claim 15, wherein the incident radiation comprises x-rays.

17. The method of claim 15, further comprising annealing the scintillator coating by heat treatment at a temperature in the range of about 100 to 1400° C.

18. A non-pixelated radiological scintillator coating material made by the method of claim 15.

19. A device for x-ray imaging, the device comprising the scintillator coating material of claim 12 and a semiconductor imaging device.

20. A device for x-ray imaging, the device comprising the scintillator coating material of claim 18 and a semiconductor imaging device.

21. The method of claim 15, resulting in preferentially oriented columnar grain growth of the scintillator coating material.

* * * * *